(12) United States Patent
Awaad et al.

(10) Patent No.: US 9,029,518 B2
(45) Date of Patent: May 12, 2015

(54) **METHOD OF EXTRACTING KAEMPFEROL-BASED ANTIOXIDANTS FROM *SOLENOSTEMMA ARGHEL***

(75) Inventors: Amani Shafeek Awaad, Riyadh (SA); Reham Moustafa El-Meligy, Riyadh (SA)

(73) Assignee: King Saud University, Riyadh (SA)

( * ) Notice: Subject to any disclaimer, the term of this patent is extended or adjusted under 35 U.S.C. 154(b) by 267 days.

(21) Appl. No.: 13/535,211

(22) Filed: Jun. 27, 2012

(65) Prior Publication Data
US 2014/0005373 A1 Jan. 2, 2014

(51) Int. Cl.
*C07H 1/08* (2006.01)
*C07H 17/07* (2006.01)

(52) U.S. Cl.
CPC . *C07H 17/07* (2013.01); *C07H 1/08* (2013.01)

(58) Field of Classification Search
CPC ..................................................... C07H 17/04
USPC ........................................................... 536/8
See application file for complete search history.

(56) References Cited

U.S. PATENT DOCUMENTS

| | | | |
|---|---|---|---|
| 5,762,936 A | 6/1998 | Ronzio et al. | |
| 6,524,625 B2 | 2/2003 | Aga et al. | |
| 2010/0113372 A1 | 5/2010 | Park et al. | |
| 2010/0136205 A1 | 6/2010 | Konishi | |
| 2010/0273726 A1 | 10/2010 | Hamann et al. | |

FOREIGN PATENT DOCUMENTS

| | | |
|---|---|---|
| CN | 101433545 A | 5/2009 |
| JP | 56135496 A | 10/1981 |
| JP | 2010248130 A | 11/2010 |
| WO | WO2004009575 A1 | 1/2004 |
| WO | WO2009036120 A1 | 3/2009 |

OTHER PUBLICATIONS

Awaad, A. S. et al., Recent Progress in Medicinal Plants, Ethnomedicine: Source & Mechanism, "Antioxidant Natural Plant", Jan. 2010, vol. 27, pp. 1-35.*
Mohamed, N. W. et al., Records of Natural Products, "Anti-ulcerogenic Activity of Extract and Some Isolated Flavonoids from *Desmostachia bipinnata* (L.) staphf", 2008, vol. 2, No. 3, pp. 76-82.*
Soltan, M. M. et al., Journal of Ethnopharmacology, "Antiviral screening of forty-two Egyptian medicinal plants", 2009, vol. 126, pp. 102-107.*
Zain, M. E. et al., Phytopharmacology, "Antimicrobial activities of Saudi Arabian desert plants", Jan. 2012, vol. 2, No. 1, pp. 106-113.*
El Hady, et al. "Studies for Determining Antimicrobial Activity of *Solenastemma argel* (Del) Hayne. 2-Extraction With Chloroform/Methanol in Different Proportions", Qatar Univ. Sci. J. (1994), 14(C), pp. 143-146.
El Hady, et al. "Studies for Determining Antimicrobial Activity of *Solenostemma argel* (Del) Hayne. 1-Extraction With Methanol/Water in Different Proportions", Qatar Univ. Sci. J. (1994), 14(C), pp. 138-142.
Hassan et al., "Pregnene derivatives from *Solenostemma argel* leaves", Phytochemistry 57 (2001), pp. 507-511.
Heneidak et al., "Flavonoid glycosides from Egyptian species of the tribe Asclepiadeae (Apocynaceae, subfamily Asclepiadoideae)", Biochemical Systematics and Ecology 34 (2006), pp. 575-584.

* cited by examiner

*Primary Examiner* — Layla Bland
*Assistant Examiner* — Bahar Craigo
(74) *Attorney, Agent, or Firm* — Richard C Litman

(57) ABSTRACT

The method of extracting kaempferol-based antioxidants from *Solenostemma arghel* provides a method of producing medicinal antioxidants for usage as anti-inflammatory and analgesic treatments. The kaempferol-based antioxidants are primarily kaempferol-3, 4'-diglucoside and kaempferol 3-rutinoside. The method includes the following steps: collecting aerial parts of *Solenostemma arghel;* drying the aerial parts; powdering the aerial parts; extracting the powdered aerial parts in ethanol and filtering to produce a filtrate; concentrating the filtrate to form a concentrated residue; dissolving the concentrated residue in water; and extracting the kaempferol-based antioxidant from the dissolved residue in ethyl acetate.

19 Claims, 8 Drawing Sheets

US 9,029,518 B2

METHOD OF EXTRACTING KAEMPFEROL-BASED ANTIOXIDANTS FROM *SOLENOSTEMMA ARGHEL*

BACKGROUND OF THE INVENTION

1. Field of the Invention

The present invention relates to a method of producing medicinal antioxidants for use as anti-inflammatory and analgesic treatments, and more particularly, to a method of extracting kaempferol-based antioxidants from *Solenostemma arghel*, more exactly, *Solenostemma arghel* (Del.) Hayne.

2. Description of the Related Art

An antioxidant is a molecule capable of inhibiting the oxidation of other molecules. Oxidation is a chemical reaction that transfers electrons from a substance to an oxidizing agent. Oxidation reactions can produce free radicals. In turn, these free radicals can start chain reactions. When the chain reaction occurs in a cell, it can cause damage or death. Antioxidants terminate these chain reactions by removing free radical intermediates, and inhibit other oxidation reactions. They do this by being oxidized themselves, so antioxidants are often reducing agents, such as thiols, ascorbic acid or polyphenols.

People who eat fruits and vegetables have a lower risk of heart disease and some neurological diseases, and there is evidence that some types of vegetables, and fruits in general, protect against some cancers. Since fruits and vegetables happen to be good sources of antioxidants, this suggests that antioxidants might prevent some types of diseases. Antioxidants are presently being investigated for a wide variety of medical treatments, including usage as anti-inflammatory substances and analgesics.

Given that antioxidants are often found naturally in fruits and vegetables, extraction methods from raw plants are of great interest. However, since plants are regional, rather than universal, it would be desirable to be able to extract antioxidants that are found in common plant life within particular regions. In the Middle East and Africa, for example, *Solenostemma arghel* (sometimes written as "argel", with a binomial name of *Solenostemma arghel* (Delile) Hayne) is a plant in the family *Apocynaceae*, which is not only relatively common, but is already in use (in its raw form) for medicinal purposes.

The leaves are used in herbal medicine for the treatment of some diseases, such as of liver and kidney and allergies. It has been found to be an effective remedy for bronchitis and is used to treat neuralgia and sciatica. Further, it is used as incense in the treatment of measles and sometimes crushed and used as remedy for suppurating wounds. The leaves may be infused to treat gastrointestinal cramps, stomachache, colic, cold and urinary tract infections, and has further been found to be effective as an anti-syphilitic if used for prolonged periods of 40-80 days. Several active compounds have been identified in *Solenostemma*, including kaempferol-based antioxidants.

Kaempferol-based antioxidants have been shown to have anti-inflammatory and analgesic properties. Thus, a method of extracting kaempferol-based antioxidants from *Solenostemma arghel* solving the aforementioned problems is desired.

SUMMARY OF THE INVENTION

The method of extracting kaempferol-based antioxidants from *Solenostemma arghel* provides a method of producing medicinal antioxidants for usage as anti-inflammatory and analgesic treatments. The kaempferol-based antioxidants are primarily kaempferol-3, 4'-diglucoside and kaempferol 3-rutinoside. The method includes the following steps: collecting aerial parts of *Solenostemma arghel*; drying the aerial parts; powdering the aerial parts; extracting the powdered aerial parts in ethanol and filtering to produce a filtrate; concentrating the filtrate to form a concentrated residue; dissolving the concentrated residue in water; and extracting the kaempferol-based antioxidant from the dissolved residue in ethyl acetate. The method may further include separating the ethyl acetate extract into portions based upon TLC $R_f$ values and color, evaporating the ethyl acetate from the portions, and recrystallizing the residue in methanol to obtain the isolated compounds.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The method of extracting kaempferol-based antioxidants from *Solenostemma arghel* relates to a method of producing medicinal antioxidants for use as anti-inflammatory and analgesic treatments, either for use in standardized extracts as nutritional supplements, or as pharmaceuticals. The kaempferol-based antioxidants are primarily kaempferol-3, 4'-diglucoside and kaempferol 3-rutinoside. First, the aerial parts of Solenostemma arghel are collected and then dried. The drying preferably is performed through air drying in shade. Once dried, the aerial parts were powdered to a fine powder, packed in tightly closed containers, and stored.

A kaempferol-based compound was then extracted from the powdered aerial parts through ethanol extraction and filtering to produce a filtrate. The ethanol extraction was performed through percolation of about 1000 g of the powdered aerial part in a 95% ethanol solution at room temperature for two days. The ethanol extract was filtered and the residues were re-percolated four times to form a concentrated residue. Concentration of the filtrate was performed under reduced pressure at a temperature of less than about 40° C. to yield about 250 g of the concentrated residue.

The concentrated residue was then dissolved in 300 ml of hot water, and then the kaempferol-based antioxidants were extracted from the dissolved residue through ether, chloroform, ethyl acetate, and butanol extraction, yielding 4.3 g, 6.2 g, 23.9 g and 45.9 g of antioxidant-containing compounds, respectively.

Silica Gel G was used for thin layer chromatography (TLC) (on pre-coated plates) and column chromatography. Three different solutions were used for developing the chromatoplates: (a) ethyl acetate-methanol-water (30:5:4); (b), ethyl acetate-methanol-acetic acid-water (65:15:10:10); and (c) chloroform-methanol (95:10). Visualization of the chromatograms was achieved under ultraviolet (UV) light before and after exposure to ammonia vapor or, alternatively, by spraying with aluminum chloride. TLC examination of the different extracts using solvent systems and visualizing reagents revealed the presence of same four spots in the ethyl acetate extracts.

Figure 5A:
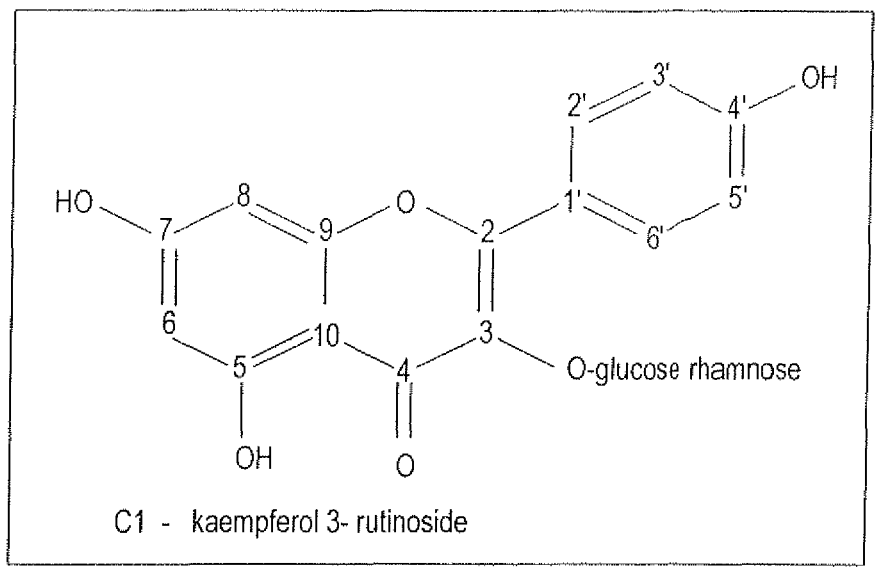
FIG. 5A is the structural formula of kaempferol 3-rutinoside (hereinafter referred to as compound $C_1$), isolated from *Solenostemma arghel* (Del.) Hayne.
Figure 5B:
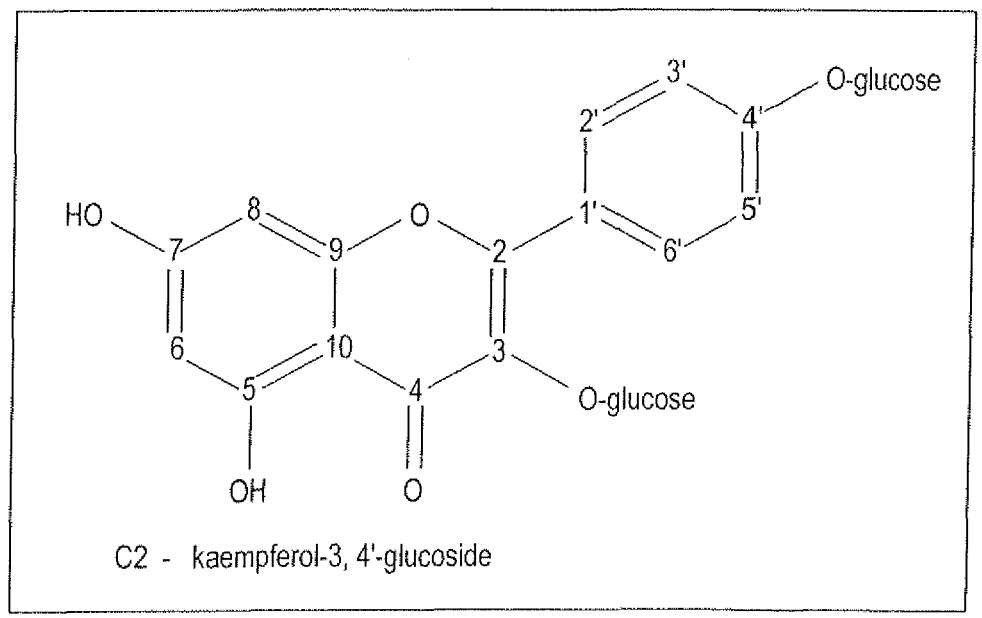
FIG. 5B is the structural formula of kaempferol-3, 4'-glucoside (hereinafter referred to as compound $C_2$), isolated from *Solenostemma arghel* (Del.) Hayne.

When the extracts (ether, chloroform, ethyl acetate and butanol) were tested for their pharmacological activities, the ethyl acetate fraction showed the highest activity as an analgesic and an anti-inflammatory substance. Thus, 20 g of the ethyl acetate fraction was applied on the top of the column chromatograph packed with silica gel (350 g) and eluted gradually with chloroform-methanol. Ninety fractions (100 ml each) were collected and reduced to three main sub-fractions in different yields of 6.4, 8.7 and 9.6, respectively (according to the number, color and $R_f$ values of the spots), and each of these sub-fractions were reapplied for preparative thin layer chromatography using solution (c) above as the developing system. A UV lamp was used for visualization for final purifications, and each flavonoid was separately eluted by methanol, concentrated and then re-purified on a column of Sephadex® LH-20 eluted by methanol-water, from which kaempferol 3-rutinoside (hereinafter referred to as compound $C_1$) and kaempferol-3, 4'-glucoside (hereinafter referred to as compound $C_2$) were isolated and crystallized from methanol (see FIG. 5A and FIG. 5B).

Total acid hydrolysis was performed with ten mg of each isolate being subjected to acid hydrolysis using 0.1 M HCl for one hour. The aqueous extract was then neutralized using barium carbonate and filtered off. The filtrate was extracted with ethyl acetate to separate the aglycone (glycoside-free) moiety from the glycone. The ethyl acetate extract was concentrated and subjected to UV shift reagents, $^1$H-NMR, and $^{13}$C-NMR. The aqueous layer (containing glycone) was tested using high performance liquid chromatography (HPLC) with a Phenomenex® $NH_2$ column with dimensions of 250 mm (length)×4.6 mm (diameter)×5 um (particle size) as a stationary phase and 0.1 M sulfuric acid as a mobile phase. Both TLC and paper chromatography (PC) were performed.

In addition to the chromatography described above, the presence and purity of compounds $C_1$ and $C_2$ was further confirmed through melting points and through mass spectrometry. For melting points, a Kofler hot-stage apparatus was utilized, and for mass spectrometry, a mass spectra (Electrospray negative ion) sample dissolved in acetonitrile was tested on a Micromass Quattro spectrometer. $^1$H and $^{13}$C NM spectra, using external electronic referencing through the deuterium resonance frequency of the solvent, were determined at 600.17 MHz and 150.91 MHz, respectively, with a JEOL ECA 600 spectrometer fitted with an auto 5 mm X/H probe. Carbon atom types were established in the $^{13}$CNMR spectrum by employing a combination of broad-decoupled, proton-decoupled and distortionless enhancement by polarization transfer (DEPT) experiments with 64,000 data points over a spectrum width of 17,605.6 Hz. ($^1J_{C-H}$ and $^2J_{C-H}$ and $^3J_{C-H}$ respectively). The $^1$H-$^{13}$C correlations were established by using heteronuclear multiple quantum coherence (HMQC) and heteronuclear multiple bond coherence (HMBC) pulse sequences, respectively. $^1$H-$^1$H correlations were performed by double quantum filtered correlation spectroscopy (COSY).

The median lethal dose ($LD_{50}$) of the total ethanol extract of Solenostemma arghel was also estimated in mice. In a preliminary test, animals in groups of three received one of 10, 100, or 1,000 mg/kg of the tested extract orally. The animals were observed for 24 hours for signs of toxicity and number of deaths. Depending on the results of the preliminary test, doses of 1,250, 2,500, and 5,000 mg/kg of the tested extract were administered to fresh groups, each of six mice. Control animals received the vehicle and were kept under the same conditions. Signs of toxicity and the number of deaths per dose were recorded within 24 hours, and the $LD_{50}$ was calculated as the geometric mean of the dose that resulted in 100% mortality and that which caused no lethality at all.

The water and total ethanol extracts of Solenostemma arghel did not produce any behavioral changes and mortality in mice in doses up to 5,000 mg/kg. Thus, it may be concluded that oral $LD_{50}$ of the total extract is higher than 5,000 mg/kg. Therefore, the tested plant can be categorized as highly safe, since substances possessing $LD_{50}$ higher than 50 mg/kg are non-toxic.

Figure 1A:
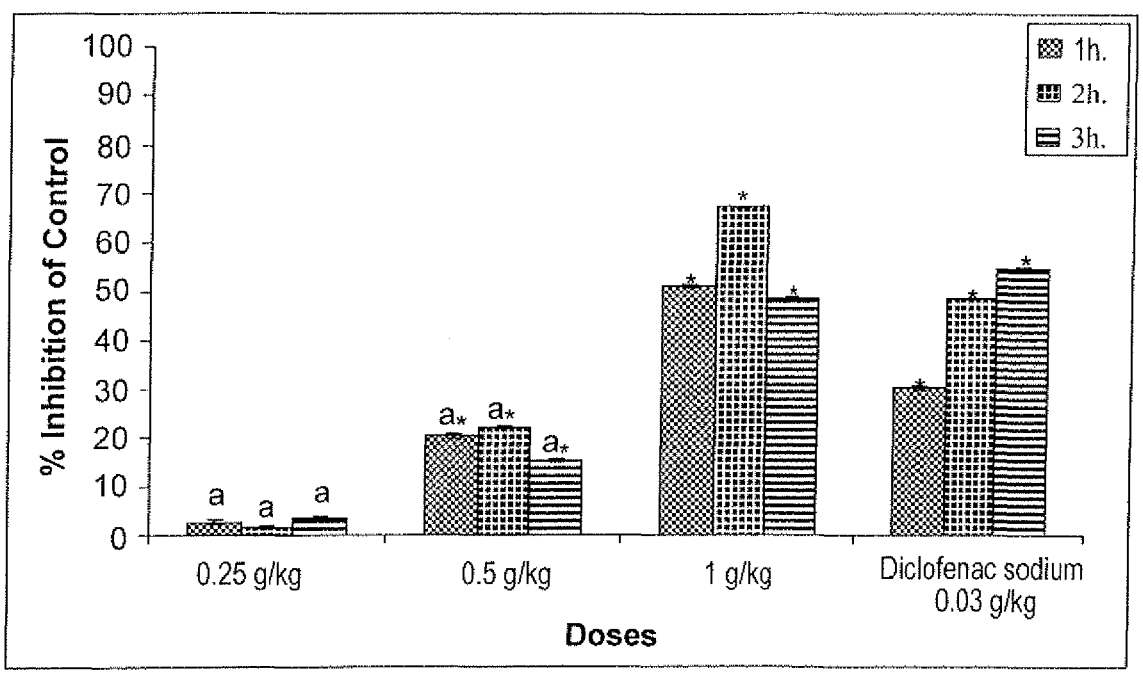
FIGS. 1A, 1B and 1C are histogram charts graphically illustrating the percentage of inhibition of edema (Odema) by various dosages of the ethanol extract (FIG. 1A), comparative fractions (0.25 g/kg) of the four extraction solvents (FIG. 1B) and isolated compounds (0.1 g/kg) (C1=kaempferol-3, 4'-diglucoside, C2=kaempferol 3-rutinoside) from *Solenostemma arghel* (FIG. 1C) after one, two and three hours, respectively, compared with diclofenac sodium (Voltaren).
Figure 1B:
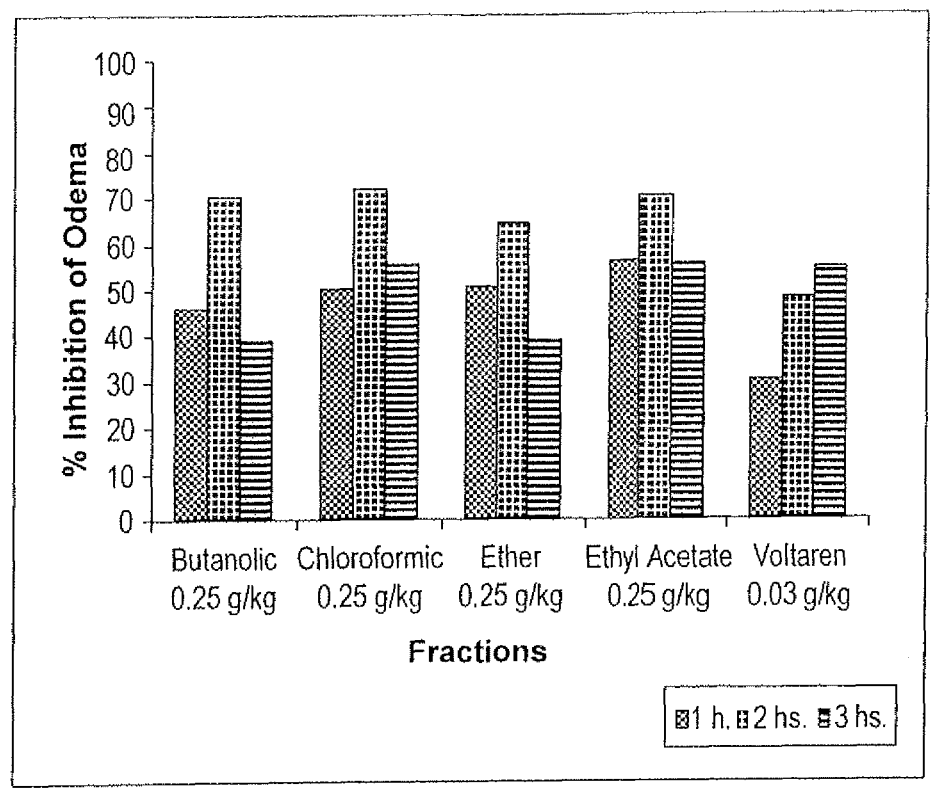
Figure 1C:
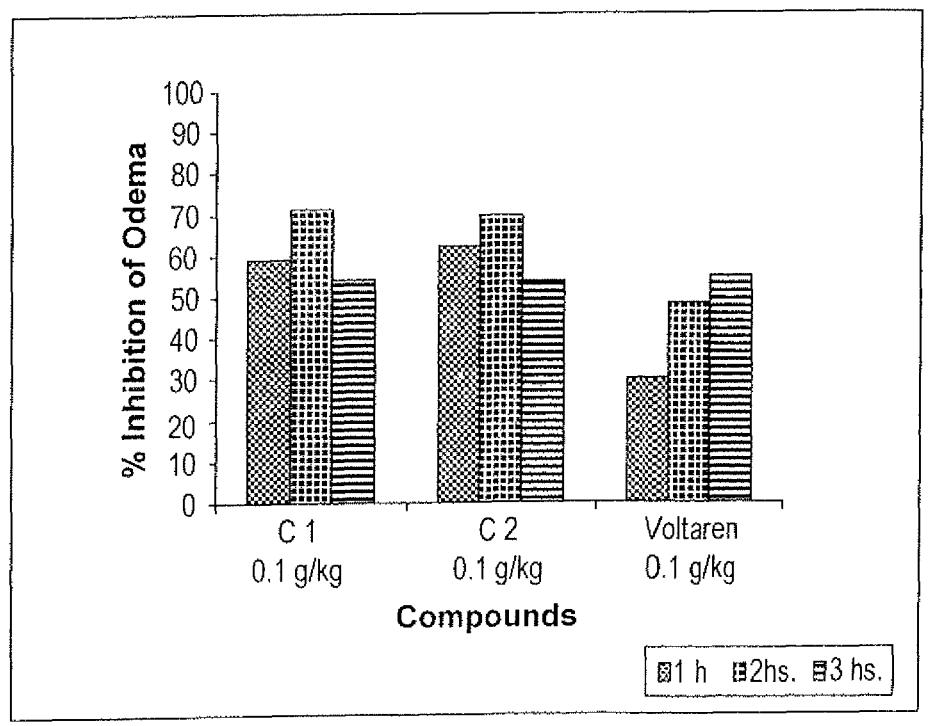

With regard to the pharmacological study of the anti-inflammatory effects of the Solenostemma arghel antioxidant extracts, the activity of all extracts (water, total ethanol, ether, chloroform, ethyl acetate, butanol, and compounds $C_1$ and $C_2$) were tested using carrageenan-induced rat paw edema. The total alcohol (ethanol) extract was given at doses of 0.25, 0.5 and 1 g/kg, respectively, and fractions were given in doses of 0.25 g/kg. Compounds were given in a dose of 0.1 g/kg. The effects of the alcohol extract, fractions and isolated compounds are shown in FIGS. 1A, 1B and 1C, respectively, and given below in Table 1. FIGS. 1A, 1B and 1C graphically illustrate the percentage of inhibition of the edema, induced by subcutaneous injection of 0.1 ml 1% carrageenan into the plantar side of the left hind paw, by ethanol extracts, by fractions (0.25 g/kg) of the different extraction solvents, and by the isolated compounds (0.1 g/kg) from Solenostemma arghel after one, two and three hours, respectively, compared with diclofenac sodium (Voltaren® ampoules, 75 mg/3 ml, from Novartis AG Corporation, Switzerland).

TABLE 1

Effects of *Solenostemma arghel* (Del.)
Hayne extracts on rat paw edema

| Extract | Dose (g/kg) | Time (h) | Paw thickness(mm) Mean ± S.D. | % inhibition of control |
|---|---|---|---|---|
| Control | 0 | 1 | 2.53 $^a$ ± 0.32 | 0 |
|  |  | 2 | 3.10 $^a$ ± 0.27 | 0 |
|  |  | 3 | 3.02 $^a$ ± 0.23 | 0 |
| Total alcohol and water extracts | 0.25 | 1 | 2.47 $^a$ ± 0.33 | 2.61 |
|  |  | 2 | 3.05 $^a$ ± 0.24 | 1.68 |
|  |  | 3 | 2.91 $^a$ ± 0.23 | 3.61 |
|  | 0.5 | 1 | 2.02 $^{a*}$ ± 0.67 | 20.33 |
|  |  | 2 | 2.42 $^{a*}$ ± 0.46 | 22.05 |
|  |  | 3 | 2.55 $^{a*}$ ± 0.45 | 15.41 |
|  | 1.0 | 1 | 1.24 * ± 0.34 | 51.13 |
|  |  | 2 | 1.02 * ± 0.16 | 67.28 |
|  |  | 3 | 1.55 * ± 0.43 | 48.62 |
| Ether | 0.25 | 1 | 1.25 * ± 0.42 | 50.65 |
|  |  | 2 | 1.10 * ± 0.14 | 64.54 |
|  |  | 3 | 1.84 * ± 0.15 | 39.01 |
| Chloroform | 0.25 | 1 | 1.26 $^{a*}$ ± 0.37 | 50.26 |
|  |  | 2 | 0.86 $^{a*}$ ± 0.12 | 72.28 |
|  |  | 3 | 1.34 $^{a*}$ ± 0.29 | 55.59 |
| Ethyl acetate | 0.25 | 1 | 1.10 $^{a*}$ ± 0.08 | 56.57 |
|  |  | 2 | 0.91 $^{a*}$ ± 0.20 | 70.66 |
|  |  | 3 | 1.34 $^{a*}$ ± 0.30 | 55.59 |
| Butanol | 0.25 | 1 | 1.36 * ± 0.44 | 46.31 |
|  |  | 2 | 0.92 * ± 0.13 | 70.34 |
|  |  | 3 | 1.84 * ± 0.14 | 39.01 |
| C1 | 0.1 | 1 | 1.04 $^{a*}$ ± 0.16 | 59.06 |
|  |  | 2 | 0.89 $^{a*}$ ± 0.14 | 71.31 |
|  |  | 3 | 1.39 * ± 0.30 | 53.93 |
| C2 | 0.1 | 1 | 0.95 $^{a*}$ ± 0.16 | 62.50 |
|  |  | 2 | 0.93 $^{a*}$ ± 0.13 | 70.02 |
|  |  | 3 | 1.40 $^{a*}$ ± 0.22 | 53.60 |
| Diclofenac sodium | 0.03 | 0 | 1.77 * ± 0.22 | 30.24 |
|  |  | 2 | 1.60 * ± 0.23 | 48.42 |
|  |  | 3 | 1.37 * ± 0.15 | 54.69 |

* Significantly different from the control at the corresponding time, at $p < 0.05$.
$^a$ Significantly different from diclofenac sodium at the corresponding time, at $p < 0.05$ Oral administration of the water and total ethanol extracts of *Solenostemma arghel* (Del.) Hayne at doses of 0.5 and 1.0 g/kg, the fractions at doses of 0.25 g/kg, and compounds at 0.1 g/kg to rats induced a significant ($P<0.05$) decrease in the thickness of the inflamed paw, which persisted for three hours. The achieved anti-inflammatory activity for total alcohol (ethanol) (1 g/kg dose) and butanol extracts was similar to that of diclofenac sodium at a dose of 0.03 g/kg. The anti-inflammatory activity of chloroform and ethyl acetate extracts and the isolated compounds were significantly ($P<0.05$) greater than that of diclofenac sodium. Further, the activity of the dose 0.5 g/kg for the total extract was significantly less than that for diclofenac sodium. The activity after two hours was found to be significantly ($P<0.05$) more potent than after one hour and three hours for all extracts.

Figure 2A:
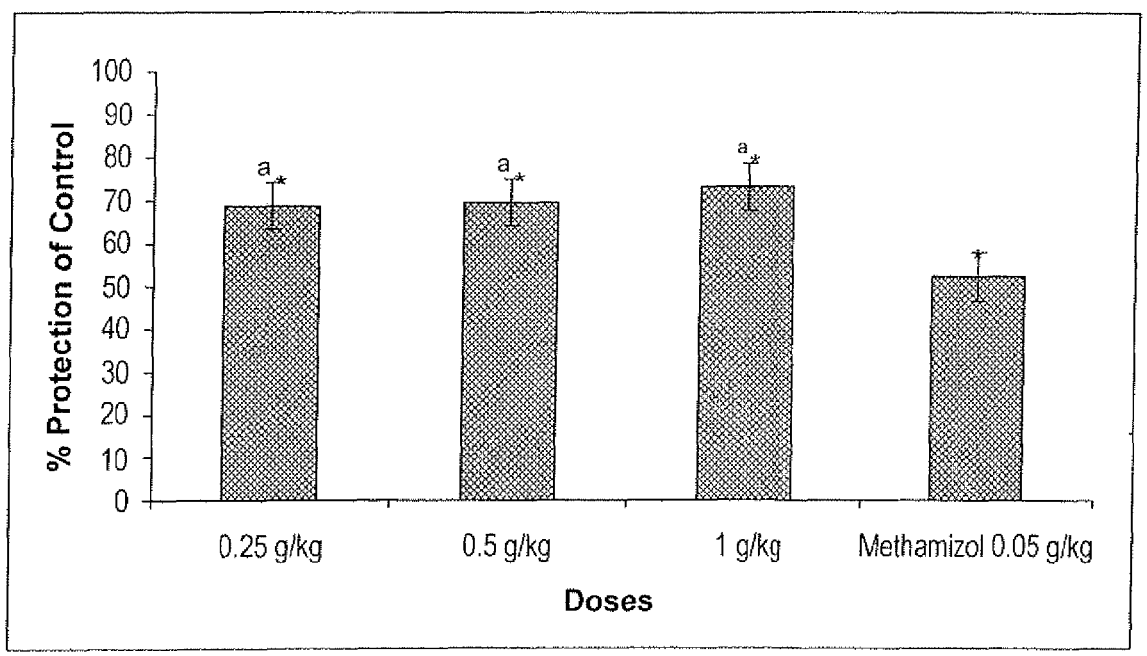
FIGS. 2A, 2B and 2C are histogram charts graphically illustrating the percentage of inhibition of writhes, induced by intraperitoneal injection of 10 ml/kg 0.7% acetic acid, by various dosages of the ethanol extract (FIG. 2A), by fractions (0.25 g/kg) of the four extraction solvents (FIG. 2B), and by the isolated compounds (0.1 g/kg) (Comp (1)=kaempferol-3, 4'-diglucoside, Comp (2)=kaempferol 3-rutinoside) from *Solenostemma arghel* (FIG. 2C) compared with methamizol (Novalgin).
Figure 2B:
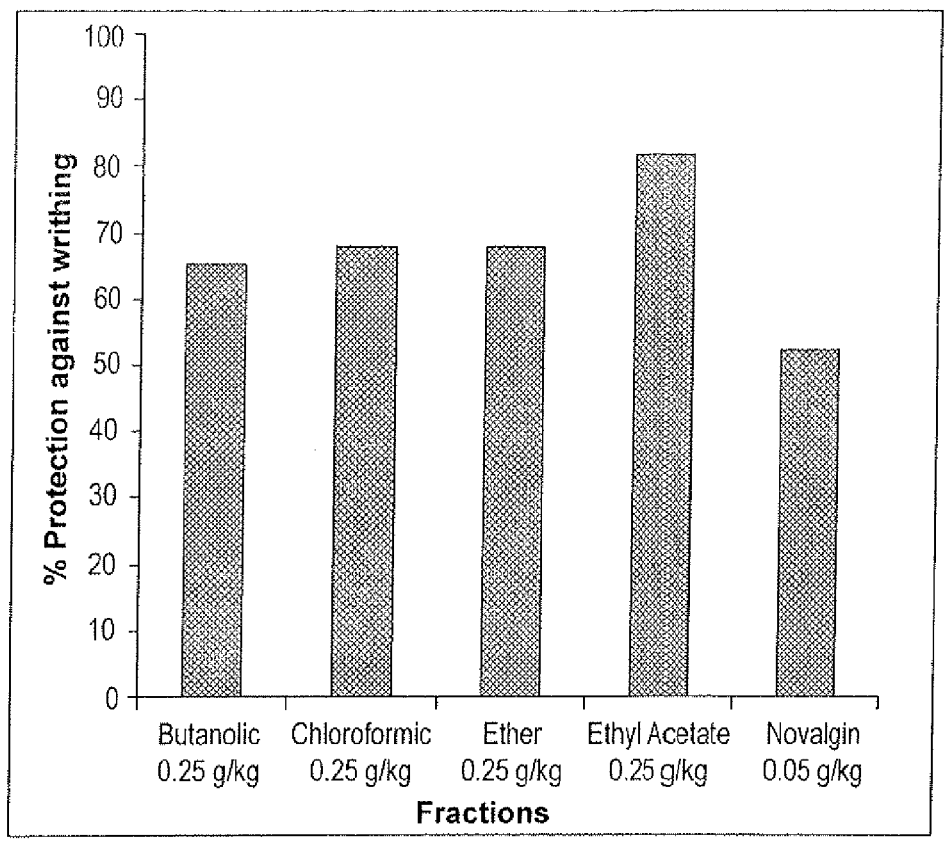
Figure 2C:
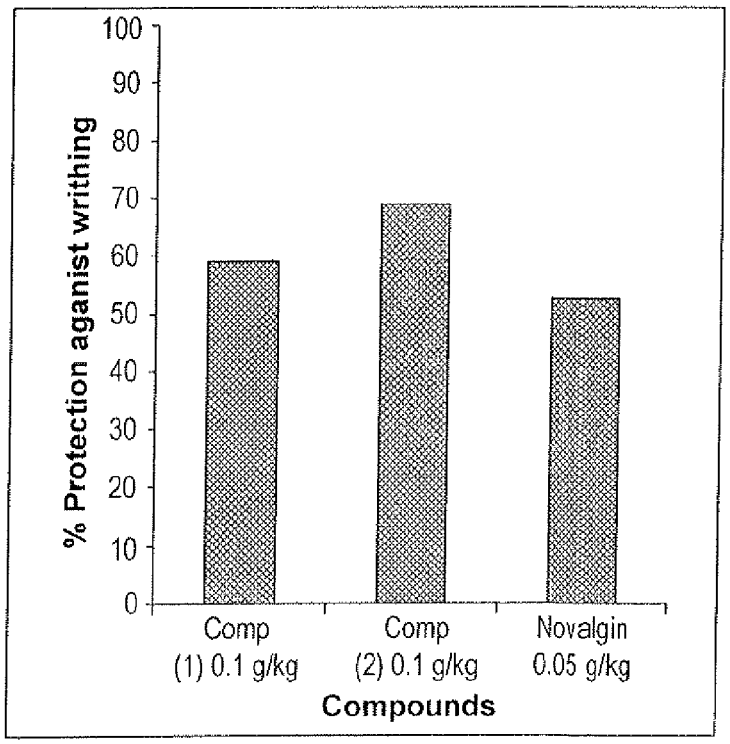

With regard to anti-nociceptive and peripheral analgesic activity, the activity of all extracts (water, total ethanol, ether, chloroform, ethyl acetate, butanol, and compounds C1 and C2) was tested using acetic acid-induced writhes in mice. The total alcohol extract (ethanol) was given at doses of 0.25, 0.5 and 1.0 g/kg, respectively; the fractions were given at doses of 0.25 g/kg; and the isolated compounds were given at doses of 0.1 g/kg. The effect of the ethanol extract, fractions and isolated compounds are shown in FIGS. 2A, 2B and 2C, respectively, and given below in Table 2. FIGS. 2A, 2B and 2C graphically illustrate the percentage of inhibition of writhes, which were induced by intraperitoneal injection of 10 ml/kg 0.7% acetic acid, by the fractions (0.25 g/kg) and isolated compounds (0.1 g/kg) from *Solenostemma arghel*, compared with methamizol (Novalgin™ ampoules, 1 g/2 ml, furnished by Aventis).

TABLE 2

Effect of *Solenostemma arghel* (Del.)
Hayne extracts on writhes in mice

| Extract | Dose g/kb | Number of writhes Mean ± S.D. | % Protection of control |
|---|---|---|---|
| Control | — | 77.60 $^a$ ± 5.44 | 0 |
| Total alcoholic and water extracts | 0.25 | 24.30 $^{a*}$ ± 6.81 | 68.69 |
|  | 0.50 | 23.70 $^{a*}$ ± 5.41 | 69.46 |
|  | 1.00 | 20.60 $^{a*}$ ± 3.41 | 73.45 |
| Ether | 0.25 | 24.90 $^{a*}$ ± 3.67 | 67.91 |
| Chloroform | 0.25 | 25.00 $^{a*}$ ± 5.35 | 67.78 |
| Ethyl acetate | 0.25 | 14.10 $^{a*}$ ± 3.45 | 81.83 |
| Butanol | 0.25 | 27.00 $^{a*}$ ± 4.03 | 65.21 |
| C1 | 0.1 | 31.82 $^{a*}$ ± 2.32 | 59.02 |
| C2 | 0.1 | 24.10 $^{a*}$ ± 2.18 | 68.90 |
| Methamizol | 0.05 | 37.00 * ± 5.89 | 52.32 |

* Significantly different from the control at $p < 0.05$
$^a$ Significantly different from methamizol at $p < 0.05$ With regard to peripheral analgesic activity, oral administration of the water and total alcohol (ethanol) extracts of *Solenostemma arghel* (Del.) Hayne at doses of 0.25, 0.5 and 1 g/kg, the fractions at a dose of 0.25 g/kg, and the isolated compounds at a dose of 0.1 g/kg, significantly ($P<0.05$) reduced the number of writhes in mice. The achieved activity for all were significantly ($P<0.05$) more effective that of methamizol at the dose of 0.05 g/kg.

Figure 3A:
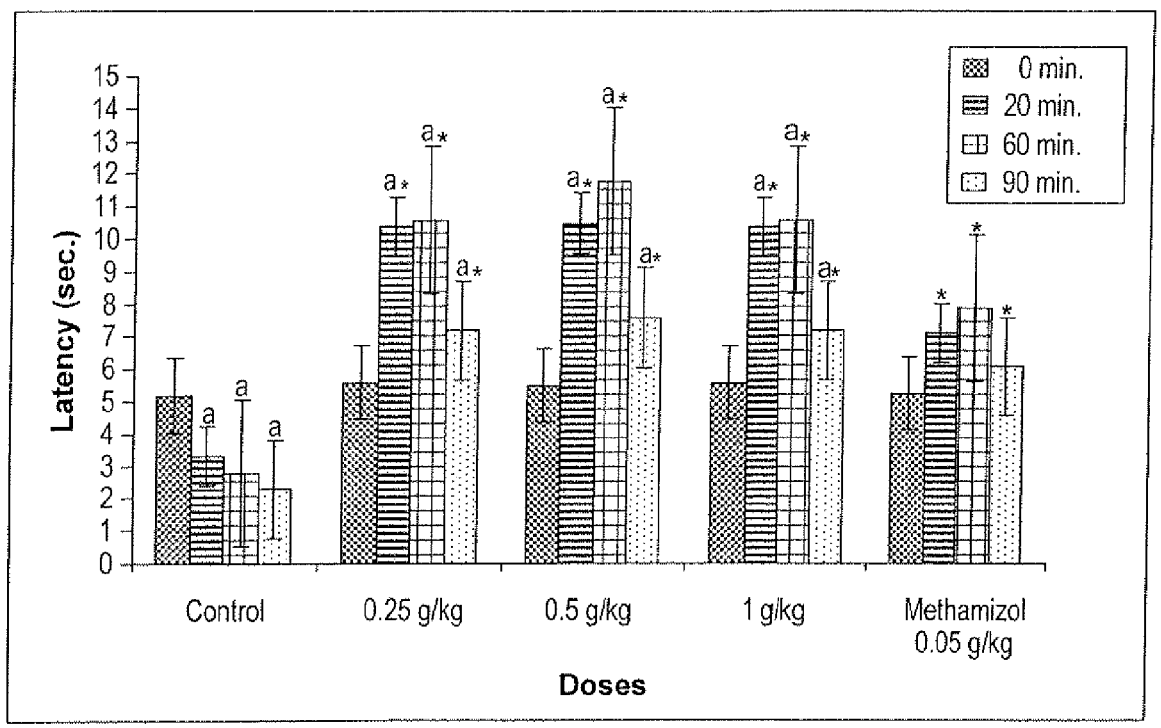
FIGS. 3A, 3B and 3C are histogram charts graphically illustrating the mean latency time (in seconds) until licking or jumping, with measurements taken 20, 60 and 90 minutes, respectively, after intraperitoneal injection of various dosages of the ethanol extract (FIG. 3A), by fractions (0.25 g/kg) of each of the four extraction solvents (FIG. 3B), and by the isolated compounds (0.1 g/kg) (C1=kaempferol-3, 4'-diglucoside, C2=kaempferol 3-rutinoside) from *Solenostemma arghel* (FIG. 3C) compared with a control group and methamizol (Novalgin).
Figure 3B:
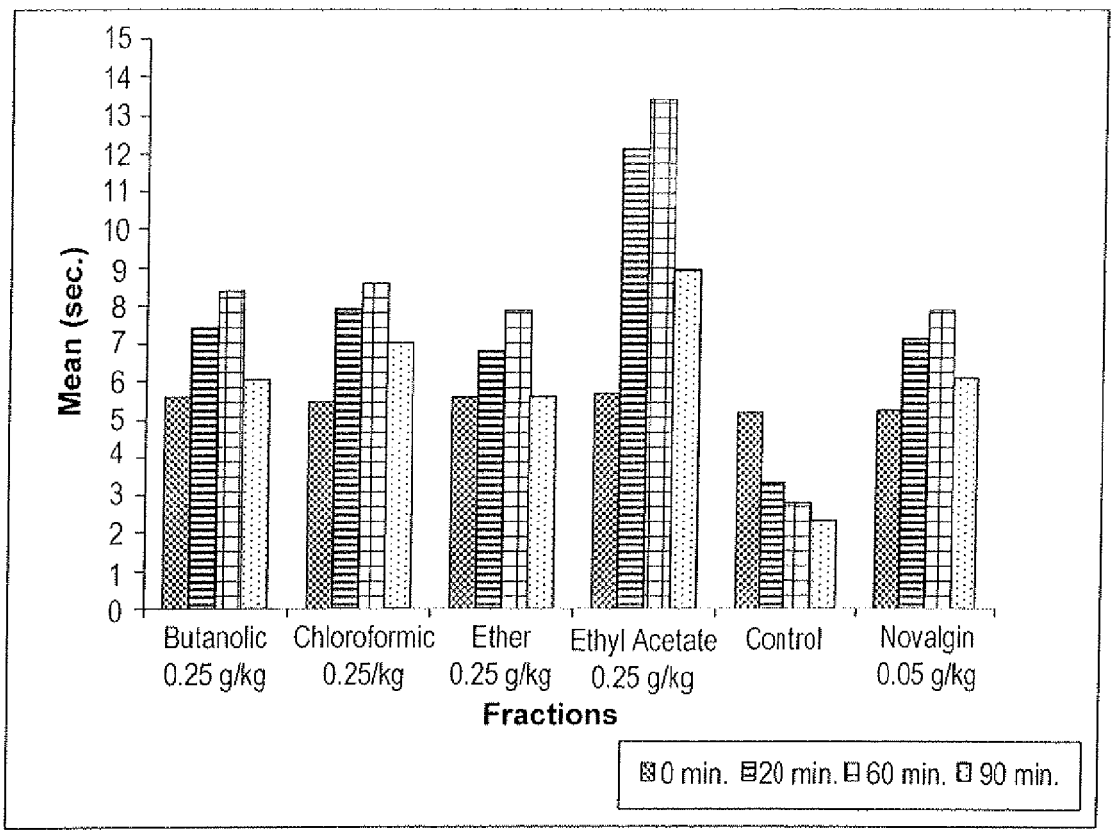
Figure 3C:
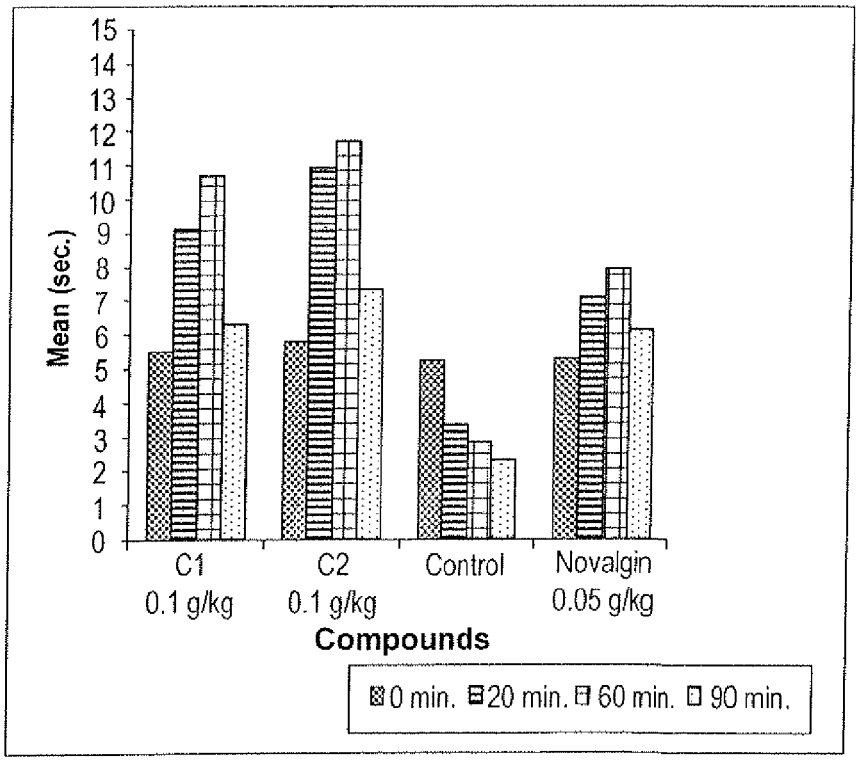

With regard to central analgesic activity, the activity of all extracts (water, total ethanol, ether, chloroform, ethyl acetate, butanol, and compounds C1, and C2) was tested using a Hot plate test technique. The total alcoholic extract was given at doses of 0.25, 0.5 and 1.0 g/kg, respectively, fractions were given at doses of 0.25 g/kg, and compounds were given at doses of 0.1 g/kg. The effect of the alcoholic extract, fractions and isolated compounds are shown in FIGS. 3A, 3B and 3C, respectively, and given below in Table 3.

TABLE 3

Effect of *Solenostemma arghel* (Del.)
Hayne extracts on murine response to heat

| Extract | Dose | Time | Latency |
|---|---|---|---|
| Control | 0 | 0 | 5.20 ± 1.14 |
|  |  | 20 | 3.30 $^a$ ± 1.42 |
|  |  | 60 | 2.80 $^a$ ± 1.23 |
|  |  | 90 | 2.30 $^a$ ± 0.48 |
| Total alcoholic and water extracts | 0.25 | 0 | 5.60 ± 0.97 |
|  |  | 20 | 10.40 $^{a*}$ ± 1.17 |
|  |  | 60 | 10.60 $^{a*}$ ± 2.32 |
|  |  | 90 | 7.20 $^{a*}$ ± 1.87 |
|  | 0.50 | 0 | 5.50 ± 1.08 |
|  |  | 20 | 10.50 $^{a*}$ ± 1.96 |
|  |  | 60 | 11.80 $^{a*}$ ± 2.25 |
|  |  | 90 | 7.60 $^{a*}$ ± 1.65 |
|  | 1.00 | 0 | 5.40 ± 0.84 |
|  |  | 20 | 10.60 $^{a*}$ ± 1.65 |
|  |  | 60 | 12.3 $^{a*}$ ± 2.16 |
|  |  | 90 | 7.70 $^{a*}$ ± 1.25 |
| Ether | 0.25 | 0 | 5.60 ± 0.70 |
|  |  | 20 | 6.80 * ± 0.92 |
|  |  | 60 | 7.90 * ± 1.20 |
|  |  | 90 | 5.60 * ± 0.97 |
| Chloroform | 0.25 | 0 | 5.50 ± 1.08 |
|  |  | 20 | 7.90 * ± 1.37 |
|  |  | 60 | 8.60 * ± 1.50 |
|  |  | 90 | 7.00 * ± 1.15 |
| Ethyl acetate | 0.25 | 0 | 5.70 ± 0.82 |
|  |  | 20 | 12.10 $^{a*}$ ± 1.66 |
|  |  | 60 | 13.40 $^{a*}$ ± 2.12 |
|  |  | 90 | 8.90 $^{a*}$ ± 0.88 |
| Butanol | 0.25 | 0 | 5.60 ± 0.97 |

TABLE 3-continued

Effect of *Solenostemma arghel* (Del.)
Hayne extracts on murine response to heat

| Extract | Dose | Time | Latency |
|---|---|---|---|
| | | 20 | 7.40 * ± 1.50 |
| | | 60 | 8.40 * ± 0.97 |
| | | 90 | 6.00 * ± 1.15 |
| C1 | 0.1 | 0 | 5.50 ± 0.85 |
| | | 20 | 9.10 $^a$ * ± 1.37 |
| | | 60 | 10.70 $^a$ * ± 1.49 |
| | | 90 | 6.30 $^a$ * ± 0.95 |
| C2 | 0.1 | 0 | 5.80 ± 0.79 |
| | | 20 | 10.90 $^a$ * ± 1.37 |
| | | 60 | 11.70 $^a$ * ± 1.42 |
| | | 90 | 7.30 $^a$ * ± 1.49 |
| Methamizol | 0.05 | 0 | 5.26 ± 0.94 |
| | | 20 | 7.10 * ± 1.52 |
| | | 60 | 7.90 * ± 1.73 |
| | | 90 | 6.10 * ± 1.97 |

* Significantly different from the control at $p < 0.05$
$^a$ Significantly different from methamizol at $p < 0.05$ FIGS. 3A, 3B and 3C graphically illustrate the mean latency time (in seconds) until licking or jumping. This was recorded with mice being placed in a glass beaker, which was placed on a hot plate, which was maintained at 55° C. Measurements were taken 20, 60 and 90 minutes, respectively, after intraperitoneal injection of fractions (0.25 g/kg) and the isolated compounds (0.1 g/kg) from *Solenostemma arghel*, compared with the control group and methamizol.

With regard to central analgesic activity, all extracts (water, total, butanol, ether, ethyl acetate and chloroform), as well as the isolated compounds, at the given doses produced a significant ($P<0.05$) increase in the latency to response of mice to hot plate thermal stimulation. This effect started after 20 min. and persisted for 90 min. after I.P. administration of the extracts. The ether, chloroform and butanol extracts were as effective as methamizol at the dose of 0.05 g/kg, while the activity produced by the total ethanol extract (0.25, 0.5 and 1 g/kg), ethyl acetate extract (0.25 g/kg) and the isolated compounds C1 and C2 (0.1 g/kg) were significantly ($P<0.05$) greater than that of methamizol.

The antipyretic activity was estimated using Brewer's yeast-induced hyperpyrexia in rats. Both water and total alcohol extracts were separately given orally at doses of 0.25, 0.5 and 1.0 g/kg, respectively. The antioxidant activity was evaluated using 2,2-diphenyl-1-picrylhydrazyl (DPPH) free radical scavenging activity. A 0.05 ml sample of the test compound was added to a methanol solution of DPPH (100 μM 2.95 ml) dissolved in methanol. The compound was added at different concentrations of 2, 4, 6, 8 and 10 mg/ml, respectively, as well as for water, and the total ethanol extracts and fractions. Concentrations of 1, 2, 3, 4 and 5 mg/ml were used for C1 and C2. Equal amounts of methanol were added to the control. Absorbance was recorded at 517 nm at regular intervals of 15 s for 5 min. Ascorbic acid (100 μM) was used as a standard.

Figure 4A:
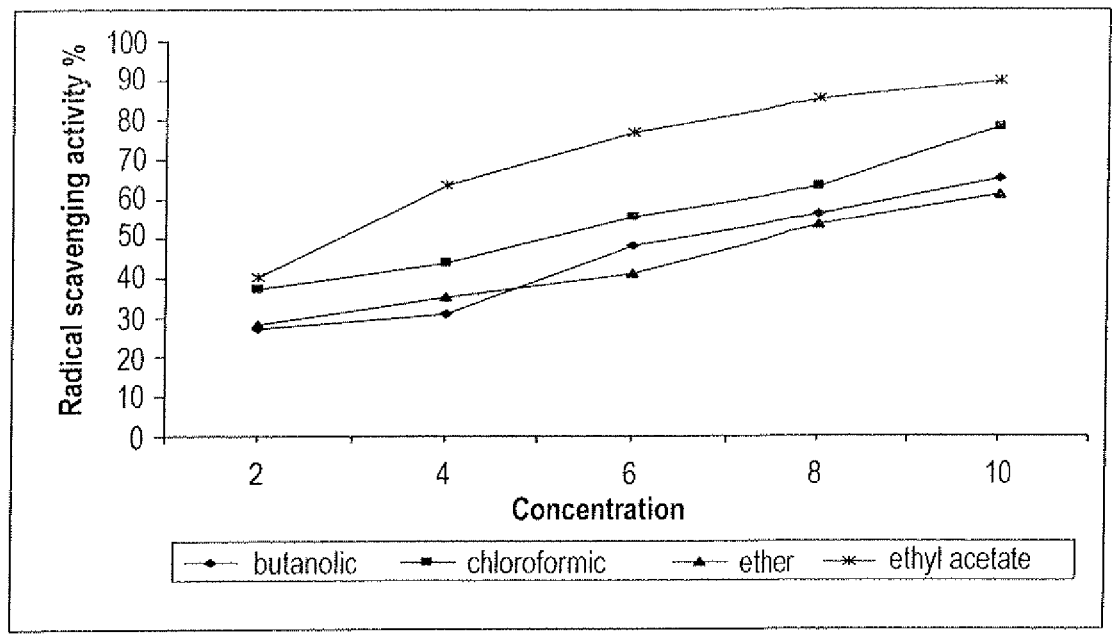
FIGS. 4A and 4B are plots illustrating the effects of fractions of each of the four extraction solvents (FIG. 4A) and of the isolated compounds (C1=kaempferol-3, 4'-diglucoside, C2=kaempferol 3-rutinoside), respectively, (FIG. 4B) from *Solenostemma arghel* (Del.) Hayne on scavenging DPPH radicals.
Figure 4B:
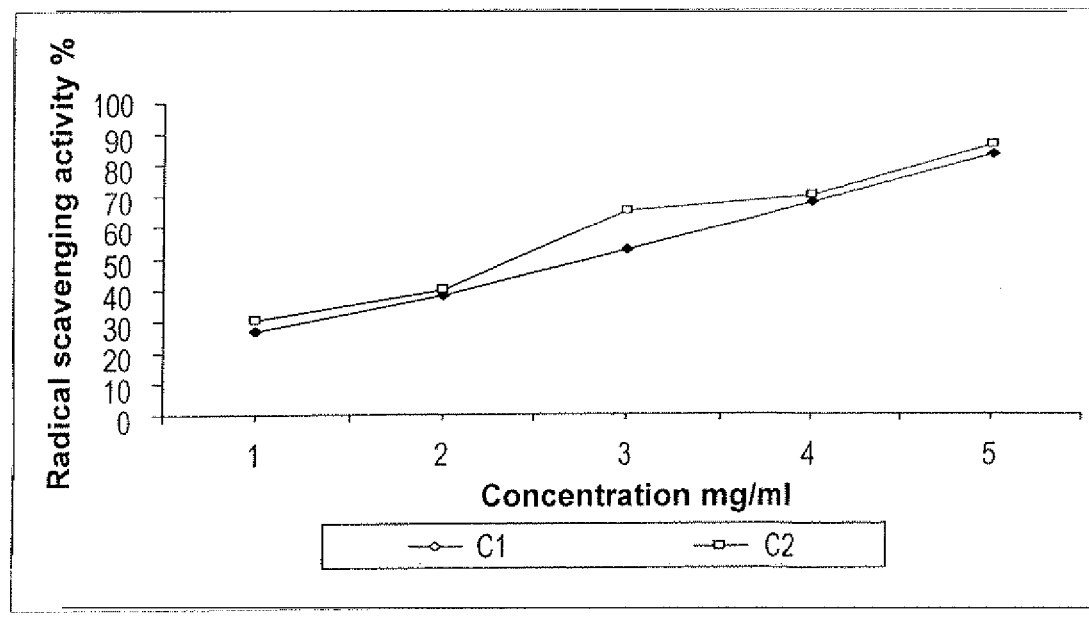

Radical scavenging activity was obtained from the following equation:

Radical scavenging activity %={$(Ac-At)/Ac$}×100, where Ac is the absorbance of control (DPPH) and At is the absorbance of the test compound (certain concentration of extract), at each measured time. The results are shown in Table 4 below, and in FIGS. 4A and 4B. It should be noted that no antipyretic activity was detected for the investigated plant at the given doses.

TABLE 4

Effect of *Solenostemma arghel* extracts
on scavenging DPPH radical

| Extract Concentration mg/ml | Radical scavenging activity (%) ± S.D. |
|---|---|
| Total ethanol and water extracts | |
| 2 | 20.00 ± 1.01 |
| 4 | 36.60 ± 1.12 |
| 6 | 54.40 ± 0.99 |
| 8 | 64.40 ± 1.05 |
| 10 | 82.40 ± 1.09 |
| Butanol | |
| 2 | 27.45 ± 1.02 |
| 4 | 31.01 ± 0.92 |
| 6 | 48.36 ± 1.01 |
| 8 | 56.33 ± 0.09 |
| 10 | 65.30 ± 0.75 |
| Chloroform | |
| 2 | 37.33 ± 1.10 |
| 4 | 43.96 ± 0.80 |
| 6 | 55.70 ± 0.99 |
| 8 | 63.20 ± 1.12 |
| 10 | 78.20 ± 0.88 |
| Ether | |
| 2 | 28.32 ± 0.80 |
| 4 | 35.42 ± 1.05 |
| 6 | 41.30 ± 1.01 |
| 8 | 53.82 ± 0.90 |
| 10 | 61.50 ± 0.09 |
| Ethyl acetate | |
| 2 | 40.26 ± 0.69 |
| 4 | 63.65 ± 0.95 |
| 6 | 76.90 ± 1.09 |
| 8 | 85.30 ± 0.99 |
| 10 | 90.30 ± 1.00 |
| C1 | |
| 1 | 26.51 ± 1.01 |
| 2 | 37.94 ± 0.98 |
| 3 | 52.63 ± 0.99 |
| 4 | 67.72 ± 1.12 |
| 5 | 83.40 ± 0.99 |
| C2 | |
| 1 | 30.28 ± 1.10 |
| 2 | 39.64 ± 0.88 |
| 3 | 65.30 ± 0.98 |
| 4 | 70.12 ± 1.01 |
| 5 | 86.50 ± 1.00 |

In biological studies, chronic oral administration of the selected plant *Solenostemma arghel* in a dose of 1 g/kg was given to animals for two weeks. A second group similarly received water orally. Blood samples were withdrawn from the retro-orbital plexus of each animal.

With regard to the effect of the water and ethanol extracts of *Solenostemma arghel* on the oxidative balance, study of the lipid peroxidation was carried out using a conventional lipid peroxidation kit. The MDA concentration was calculated as:

MDA conc.=$A$ sample×36 nmol/ml.

The concentration of MDA also can be determined from standard curves commonly found in the literature and provided with test kits. The results are shown below in Table 5.

Reduced glutathione was similarly estimated as:

In blood: concentration of *GSH* μmol/ml=[($A$+ 0.0092)/0.1374]×100

In tissue: concentration of *GSH* μmol/g=[($A$+0.0092)/ 0.1374]×100

The results are similarly shown in Table 5.

The effect of the water and total ethanol extracts of *Solenostemma arghel* on liver functions, determination of serum transaminases (ALT & AST), determination of serum alanine aminotransferase (ALT), and determination of serum aspartate aminotransferase (AST) were all also similarly determined, and the results are shown below in Table 5.

The effects of the water and total ethanol extracts of *Solenostemma arghel* on kidney functions were also studied. Determination of blood urea was carried out using conventional methods and a conventional kit, as with the above determinations. Urea concentration was calculated from the following equation:

Urea concentration (mg/dl)=($A$ sample)/($A$ St.)×50, where A is the absorbance, and A St. represents the A standard. These results are also shown below in Table 5.

Similarly, the determination of serum creatinine was carried out using a conventional method and conventional test kit. The concentration of creatinine is calculated as A2−A1=A, with:

Concentration of creatinine in serum (mg/dl)=($A$ sample)/($A$ St.)×2, where A represents absorbance, and A St. represents the A standard. These results are also given below in Table 5.

In Table 5, two groups of animals (each of 10 rats) were used, and the first group received total alcoholic extract of *Solenostemma arghel* at a dose of 1 g/kg daily for two weeks. The second group similarly received water orally. Then, the different biological parameters were measured. For statistical analysis, all values were expressed as mean±S.D. Comparisons between means were carried out using different statistical tests according to the determined parameter. Analysis of variances was carried out in two ways: using the ANOVA test followed by the Tukey HSD test using SPSS, version 14.

tial of C1 and C2 could be due to their flavonoid structure. It should be noted that the water and ethanol total extract at the dose of 1 g/kg used daily for two weeks did not show any alterations on the above-mentioned parameters.

From the above results, it can be concluded that the use of total or successive extracts is biologically better than the use of isolated compounds, since the activity of C1 and C2 alone was less than the activity of the ethyl acetate successive extract.

With regard to antioxidant activity (in vitro), all extracts were tested at concentrations of 2, 4, 6, 8 and 10 mg/ml. They showed strong scavenging activity towards DPPH radicals in a dose-dependent manner. The activity was found to be maximum at a concentration of 10 mg/ml, and reached 82.4%, 61.5%, 78.2%, 90.01% and 65.3% for water, total ethanol, ether, chloroform, ethyl acetate and butanol extracts, respectively, corresponding to 87.8% for standard ascorbic acid at a concentration of 100 μM. In addition, both compounds were tested at concentrations of 1, 2, 3, 4 and 5 mg/ml, and also showed strong scavenging activity towards DPPH radical in a dose dependant manner, the activity was maximum at concentration 5 mg/ml. It reached 83.40% and 86.50% for C1 and C2, respectively, corresponding to 87.8% for standard ascorbic acid at a concentration of 100 μM.

In the biological studies, no significant difference was observed between the control and test groups in all experiments at the 0.05 level of probability. With regard to the active compounds, the isolated compounds were identified by interpretation of their UV, $^1$H-NMR and $^{13}$C-NMR data, and were compared against the scientific literature. The compound C1 was obtained as yellow crystals from methanol, having a melting point of 342-43° C. The UV spectrum (after addition of sodium acetate) led to a bathochromic shift in band II (5 nm), indicating a free 7-OH group, which was confirmed by the appearance of a shoulder at 325 nm upon the addition of

TABLE 5

Effect of *Solenostemma arghel* (Del.) Hayne extracts on biological activities

| | Parameter Mean ± S.D. | | | | | | |
|---|---|---|---|---|---|---|---|
| | Liver function (U/l) | | Kidney function (mg/dl) | | Lipid peroxidation in | GSH in blood | GSH in tissue |
| Treatment | AST | ALT | Blood urea | Creatinine | blood (nmol/ml) | (μmol/ml) | (μmol/g) |
| Control | 18.20 ± 2.28 | 17.40 ± 2.6 | 57.00 ± 2.73 | 0.76 ± 0.07 | 27.49 ± 2.9 | 58.68 ± 4.5 | 4.64 ± 0.83 |
| Total ethanol and water extracts (1 g/kg) | 19.40 ± 2.5 | 16.00 ± 2 | 67.00 ± 3.24 | 0.68 ± 0.05 | 25.65 ± 3.8 | 51.92 ± 4.1 | 3.79 ± 0.72 |

As described above, in order to emphasis the anti-inflammatory, antinociceptive and antioxidant activities of the water and total ethanol extract of *Solenostemma arghel*, successive extracts were carried out. Four successive extracts (ether, chloroform, ethyl acetate and butanol) were obtained and showed different potentials of the reported pharmacological actions. The ethyl acetate successive extract was shown to be the most effective.

Two flavonoids, C1 (kaempferol-3, 4'-diglucoside) and C2 (kaempferol-3-rutinoside), were isolated from the ethyl acetate successive extract. Results revealed that C1 and C2 were potent anti-inflammatory and antinociceptive agents. Since both compounds C1 and C2 possessed high antioxidant potential, it is suggested that the reported anti-inflammatory and analgesic properties accompanied by antioxidant potensodium acetate. No shift was produced in band I upon the addition of sodium acetate/boric acid (the absorbance of 3, 4'-dihydroxyl group in ring B). The bathochromic shift in band I with AlCl$_3$/HCl (47 nm) indicates the presence of a free OH group and a substituent OH group at position 3, and the $^1$H-NMR and $^{13}$C-NMR results confirmed the UV results. The acid hydrolysis yielded kaempeferol as aglycone and glucose as attached glycoside, thus the compound was identified as kaempferol-3, 4'-diglucoside.

Compound C2 was obtained as yellow crystals from methanol having a melting point of 257-58° C., was soluble in methanol, and gave positive results with a Molisch test. The UV spectrum analysis in methanol (after addition of different shift reagents), showed the flavonoid nature of this compound. Λ max (band I at 336 nm and band II at 271 nm)

indicates a flavonol with substitution at C-3. Also, the addition of sodium methoxide resulted in bathochromic shift with a decrease in intensity of band I of +64 nm, indicating the presence of free hydroxyl groups. $^1$H-NMR and $^{13}$C-NMR indicated the presence of kaempeferol substituted at 3 by two sugars, and these sugars were identified after hydrolysis by HPLC, from which this compound was shown to be kaempferol-3-rutinoside.

It is to be understood that the present invention is not limited to the embodiments described above, but encompasses any and all embodiments within the scope of the following claims.

We claim:

1. A method of extracting kaempferol-3, 4'-diglucoside from *Solenostemma arghel*, comprising the steps of:
    collecting aerial parts of *Solenostemma arghel*;
    drying the aerial parts;
    powdering the aerial parts;
    extracting the powdered aerial parts in ethanol and filtering to produce a filtrate;
    concentrating the filtrate to form a concentrated residue;
    dissolving the concentrated residue in water; and
    extracting kaempferol-3, 4'-diglucoside from the dissolved residue in ethyl acetate, and
    isolating kaempferol-3, 4'-diglucoside.

2. The method of extracting kaempferol-3, 4'-diglucoside from *Solenostemma arghel* as recited in claim 1, wherein said step of drying the aerial parts comprises air drying the aerial parts in shade.

3. The method of extracting kaempferol-3, 4'-diglucoside from *Solenostemma arghel* as recited in claim 2, wherein the step of extracting the powdered aerial parts in ethanol comprises extracting about 1000 g of the powdered aerial part in a 95% ethanol solution.

4. The method of extracting kaempferol-3, 4'-diglucoside from *Solenostemma arghel* as recited in claim 3, wherein the ethanol extraction comprises percolating the powdered aerial part in the 95% ethanol solution.

5. The method of extracting kaempferol-3, 4'-diglucoside from *Solenostemma arghel* as recited in claim 4, wherein the aerial part is percolated in the 95% ethanol solution at room temperature for about two days.

6. The method of extracting kaempferol-3, 4'-diglucoside from *Solenostemma arghel* as recited in claim 5, wherein the step of concentrating the filtrate comprises concentration under reduced pressure at a temperature of less than 40° C. to yield about 250 g of the concentrated residue.

7. The method of extracting kaempferol-3, 4'-diglucoside from *Solenostemma arghel* as recited in claim 6, further comprising re-percolation of the filtrate in the 95% ethanol solution.

8. The method of extracting kaempferol-3, 4'-diglucoside from *Solenostemma arghel* as recited in claim 7, wherein the step of dissolving the concentrated residue comprises dissolving the concentrated residue in about 300 ml of water.

9. A method of extracting kaempferol 3-rutinoside from *Solenostemma arghel*, comprising the steps of:
    collecting aerial parts of *Solenostemma arghel*;
    drying the aerial parts;
    powdering the aerial parts;
    extracting the powdered aerial parts in ethanol and filtering to produce a filtrate;
    concentrating the filtrate to form a concentrated residue;
    dissolving the concentrated residue in water; and
    extracting kaempferol 3-rutinoside from the dissolved residue in ethyl acetate, and
    isolating kaempferol 3-rutinoside.

10. The method of extracting kaempferol 3-rutinoside from *Solenostemma arghel* as recited in claim 9, wherein said step of drying the aerial parts comprises air drying the aerial parts in shade.

11. The method of extracting kaempferol 3-rutinoside from *Solenostemma arghel* as recited in claim 10, wherein the step of extracting the powdered aerial parts in ethanol comprises extracting about 1000 g of the powdered aerial part in a 95% ethanol solution.

12. The method of extracting kaempferol 3-rutinoside from *Solenostemma arghel* as recited in claim 11, wherein the ethanol extraction comprises percolating the powdered aerial part in the 95% ethanol solution.

13. The method of extracting kaempferol 3-rutinoside from *Solenostemma arghel* as recited in claim 12, wherein the aerial part is percolated in the 95% ethanol solution at room temperature for about two days.

14. The method of extracting kaempferol 3-rutinoside from *Solenostemma arghel* as recited in claim 13, wherein the step of concentrating the filtrate comprises concentration under reduced pressure at a temperature of less than 40° C. to yield about 250 g of the concentrated residue.

15. The method of extracting kaempferol 3-rutinoside from *Solenostemma arghel* as recited in claim 14, further comprising re-percolation of the filtrate in the 95% ethanol solution.

16. The method of extracting kaempferol 3-rutinoside from *Solenostemma arghel* as recited in claim 15, wherein the step of dissolving the concentrated residue comprises dissolving the concentrated residue in about 300 ml of water.

17. A method of extracting kaempferol-based antioxidants from *Solenostemma arghel*, comprising the steps of:
    collecting aerial parts of *Solenostemma arghel*;
    drying the aerial parts;
    powdering the aerial parts;
    extracting the powdered aerial parts in ethanol and filtering to produce a filtrate;
    concentrating the filtrate to form a concentrated residue;
    dissolving the concentrated residue in water; and
    extracting a kaempferol-based antioxidant from the dissolved residue in ethyl acetate, and
    isolating the kaempferol-based antioxidant, wherein
    the step of extracting the powdered aerial parts comprises extracting about 1000 g of the powdered aerial part in a 95% ethanol solution.

18. The method of extracting kaempferol-based antioxidants from *Solenostemma arghel* as recited in claim 17, wherein said step of drying the aerial parts comprises air drying the aerial parts in shade.

19. The method of extracting kaempferol-based antioxidants from *Solenostemma arghel* as recited in claim 17, wherein the step of concentrating the filtrate comprises concentration under reduced pressure at a temperature of less than 40° C. to yield about 250 g of the concentrated residue, and wherein the step of dissolving the concentrated residue comprises dissolving the concentrated residue in about 300 ml of water.

* * * * *